US00PP23742P2

(12) United States Plant Patent
Creech et al.

(10) Patent No.: US PP23,742 P2
(45) Date of Patent: Jul. 16, 2013

(54) ***PRUNUS* TREE NAMED 'PURPLE PRIDE'**

(50) Latin Name: ***Prunus* hybrid**
Varietal Denomination: Purple Pride

(75) Inventors: David Creech, Nacogdoches, TX (US); Dawn Stover, Nacogdoches, TX (US)

(73) Assignee: Stephen F. Austin State University, Nacogdoches, TX (US)

( * ) Notice: Subject to any disclaimer, the term of this patent is extended or adjusted under 35 U.S.C. 154(b) by 78 days.

(21) Appl. No.: 13/373,309

(22) Filed: Nov. 9, 2011

(51) Int. Cl.
*A01H 5/00* (2006.01)

(52) U.S. Cl.
USPC ..... Plt./180

(58) Field of Classification Search
USPC ..... Plt./180
See application file for complete search history.

*Primary Examiner* — Annette Para
(74) *Attorney, Agent, or Firm* — Penny J. Aguirre

(57) ABSTRACT

A new cultivar of *Prunus*, 'Purple Pride', characterized by its foliage that is deep burgundy in color with new leaves emerging bright dark red and foliage coloration that is retained from spring through fall, its foliage that appears clean and disease free, its stems that can be readily trained into a single trunk, its white flowers that are conspicuous against its burgundy foliage, its consistent abundant crop of red fruit with a pleasing taste, its drought resistance, and is usefulness when planted in wildlife food plots in the south as the burgundy foliage allows land managers to easily recognize 'Purple Pride' plants in a brushland and avoid them during mowing regimes.

2 Drawing Sheets

Botanical classification: *Prunus* hybrid.
Variety denomination: 'Purple Pride'.

BACKGROUND OF THE INVENTION

The present invention relates to a new and distinct cultivar of *Prunus* of hybrid origin and will be referred to hereafter by its cultivar name, 'Purple Pride'. 'Purple Pride' is a new Chickasaw plum tree grown for use as a landscape plant.

The new cultivar of plum tree, 'Purple Pride', was discovered by the inventors in Nacogdoches, Tex. as a seedling that arose from seed collected and grown from *Prunus angustifolia* 'Guthrie' (not patented). The pollen parent is unknown, however it is presumed to be a different unknown species based on the characteristics of 'Purple Pride'. 'Purple Pride' was selected as a single unique plant in 2007.

Asexual reproduction of the new cultivar was first accomplished by softwood cuttings by one of the inventors in Nacogdoches, Tex. in June 2007. The characteristics of this cultivar have been determined to be stable and are reproduced true to type in successive generations.

SUMMARY OF THE INVENTION

The following traits have been repeatedly observed and represent the characteristics of the new cultivar as grown outdoors in a test plot in Nocogdoches, Tex. These attributes in combination distinguish 'Purple Pride' as a unique cultivar of *Prunus*.

1. 'Purple Pride' exhibits foliage that is deep burgundy in color with new leaves emerging bright dark red. The foliage coloration is retained from spring through fall.
2. 'Purple Pride' exhibits foliage that appears clean and disease free.
3. 'Purple Pride' can be readily trained into a single trunk.
4. 'Purple Pride' exhibits white flowers that are conspicuous against the burgundy foliage.

5. 'Purple Pride' produces a crop of red fruit with a pleasing taste.
6. 'Purple Pride' has shown to be highly drought resistant.
7. 'Prunus Pride' is useful when planted in wildlife food plots in the south as the burgundy foliage allows land managers to easily recognize 'Purple Pride' plants in a brushland and avoid them during mowing regimes.

'Guthrie', the seed parent of 'Purple Pride', differs from 'Purple Pride' in lacking burgundy colored foliage. 'Purple Pride' can be most closely compared to plants of *Prunus cerasifera*, known under the common name of Purpleleaf plum (not patented). Purpleleaf plum is similar to 'Purple Pride' in its ability to be readily formed into a single trunk (tree form) and in having foliage that is burgundy in color. Purpleleaf plum differs from 'Purple Pride' in having foliage that has much less retention of the burgundy coloration of the foliage throughout the growing season, in having fruit that is small and tasteless, and in being more prone to diseases which often results in early defoliation in the fall. 'Purple Pride' can be compared to *Prunus cerasifera* 'Thundercloud' (not patented), which differs most significantly in having a rounded form and in being a larger tree.

BRIEF DESCRIPTION OF THE DRAWINGS

The accompanying colored photographs illustrates the overall appearance and distinct characteristics of the new *Prunus*. The plants and plant parts in the photographs were taken of a 3 year-old plant of 'Purple Pride'.

The photograph in FIG. 1 provides a view of the habit and foliage coloration of 'Purple Pride'.

Figure 1:
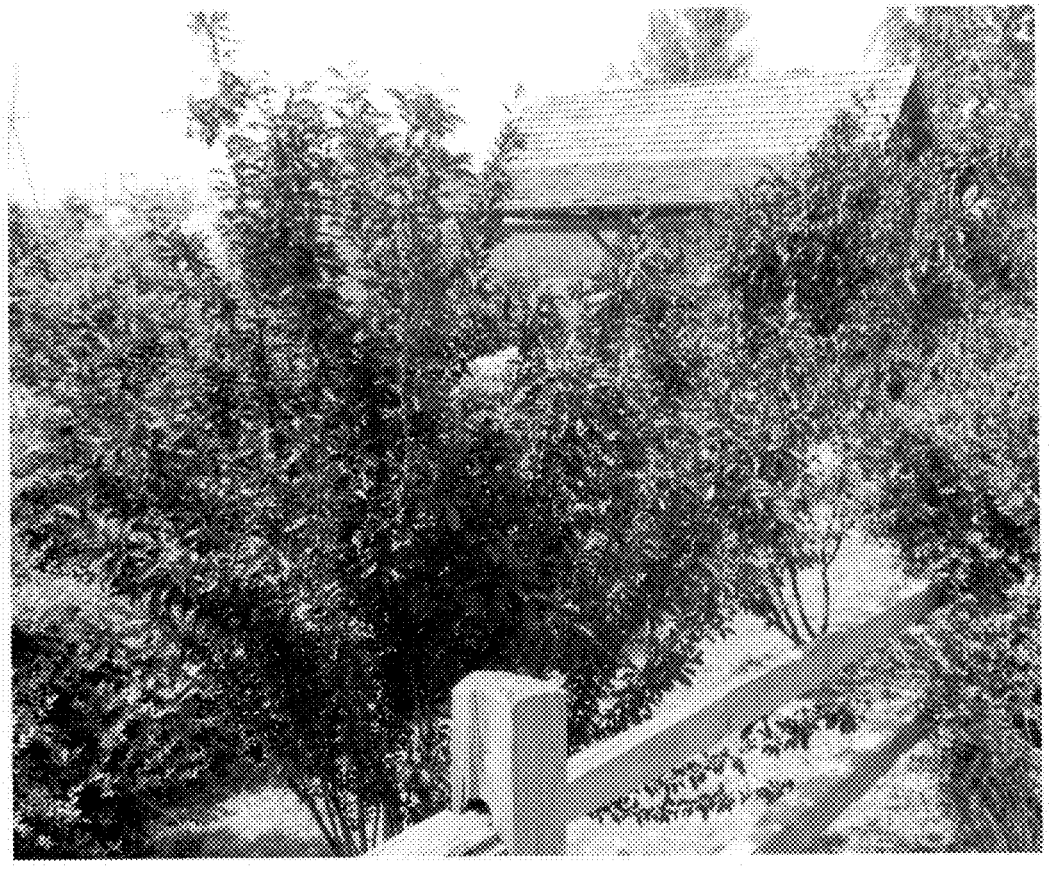
Figure 2:
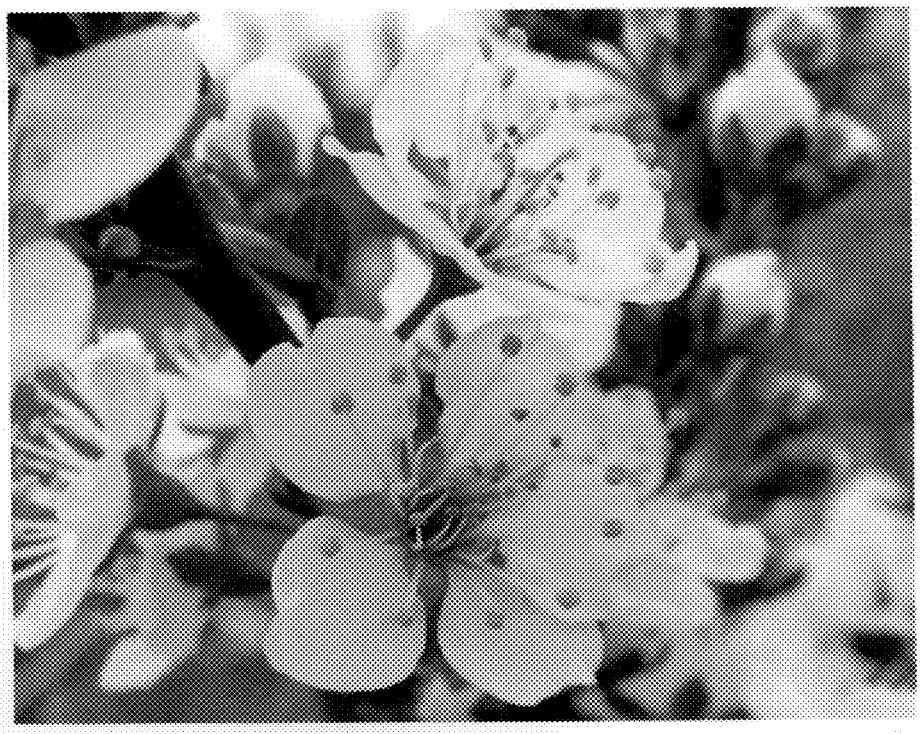

The photograph in FIG. 2 provides a close-up view of the flowers of 'Purple Pride'.

Figure 3:
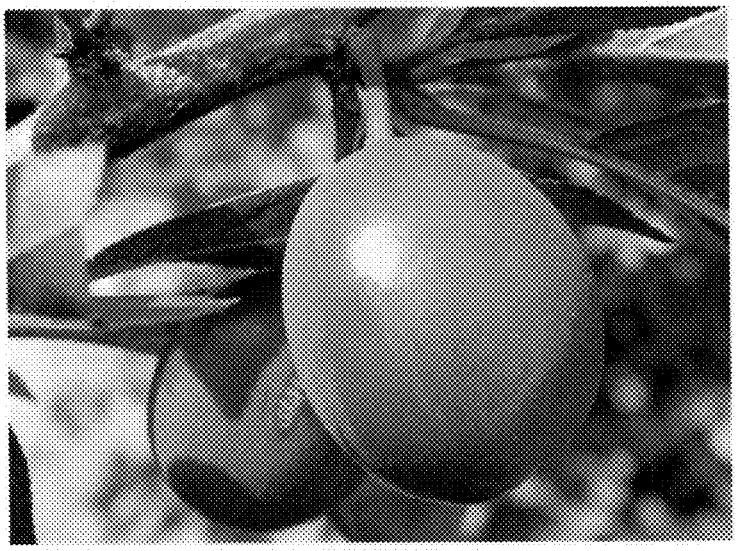

The photograph in FIG. 3 provides a close-up view of the fruit of 'Purple Pride'.

The colors in the photograph are as close as possible with the digital photography techniques available, the color values cited in the detailed botanical description accurately describe the colors of the new *Prunus.*

DETAILED BOTANICAL DESCRIPTION

The following is a detailed description of 4 year-old trees of the new cultivar as grown outdoors in Nacogdoches, Tex. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Approximately 3 weeks in March in Nacogdoches, Tex.

*Plant habit.*—Upright, readily formed into a single truck (tree form), vase-shaped, dense foliage.

*Height and spread.*—Has been observed to reach about 3 m (10 ft) in height and about 4.5 m in width (15 ft.).

*Cold hardiness.*—At least in U.S.D.A. Zone 7.

*Diseases and pests.*—Has been observed to have clean, disease free foliage.

*Environmental stresses.*—Shown to be highly drought resistant.

*Root description.*—Fibrous, freely branched.

*Propagation.*—Softwood stem cuttings, several cutting propagation trials with cuttings taken in June has resulted in over 90% successful rooting.

*Growth rate.*—Vigorous.

Stem description:

*Shape.*—Slightly oval.

*Stem color.*—New growth 146B and suffused with 165A, mature wood; 146A and suffused with 165A.

*Stem size.*—Main branches; an average about 5.66 cm in diameter and 441.96 cm in length, lateral branches; an average about 3.02 cm in diameter and 213.36 cm in length.

*Stem surface.*—New growth and mature stems; glabrous, slightly glaucous, lenticels 161C in color.

*Branching habit.*—Multiple upright lateral stems from upright main stems.

Foliage description:

*Leaf shape.*—Elliptic.

*Leaf division.*—Simple.

*Leaf base.*—Cuneate.

*Leaf apex.*—Acuminate.

*Leaf fragrance.*—None.

*Leaf venation.*—Pinnate, upper surface same as leaf color, lower surface 195B.

*Leaf margins.*—Finely crenate with minute mucronate tips on lobes.

*Leaf arrangement.*—Alternate.

*Leaf attachment.*—Petiolate.

*Leaf surface.*—Glabrous and satiny on upper and lower surface.

*Leaf size.*—Mature leaves average 6.5 cm in length and 3.5 cm in width.

*Leaf internodes.*—Average of 1.5 cm.

*Leaf color.*—Newly expanded leaves upper and lower surface; between a blend of 183B and 184B and becoming a blend of 147A blushed with 166A on upper surface and 166A on lower surface, mature leaves upper surface; 147A, mature leaves lower surface; a blend of 147B and 166A, fall leaves upper and lower surface (when grown in full sun); 187A with coloration is retained late in the season.

*Petioles.*—New leaves; an average of 7 cm in length and 1 mm in width, 146B to 146C in color, slightly pubescent surface with very short hairs.

*Stipules.*—2 per leaf, mature growth; average of 7 mm in length and 3 mm in width, ovate-lanceolate in shape, a blend of 147A blushed with 166A in color, new growth; linear-oblanceolate, about 5 mm in length and 1.5 mm in width, slightly serrated margins, cuneate base, acuminate apex, 147A in color and suffused with 166A.

Inflorescence description:

*Inflorescence type.*—Single flowers, 1 to 4 (most typically in pairs) at nodes on upper nodes of branches.

*Inflorescence size.*—Average of 1.8 cm in length and 3.5 cm in width (if 3 flowered).

*Flower buds.*—Oblanceolate, up to 4.5 cm in length and 3 cm in width prior to opening, 69C in color with upright sepals 183A in color.

*Flower fragrance.*—None detected.

*Flower quantity.*—About 40 per branch 25 cm in length.

*Flower aspect.*—Variable, from upright to nodding.

*Flower type.*—Rotate corolla above an elongated calyx with stamens and pistil extended when fully open.

*Flower size.*—Average of 1.8 cm in diameter and 6 mm in depth (without pistils and stamens).

*Calyx.*—Comprised of sepals fused into an ovoid base with un-fused portions spreading at apex, 3 mm in depth and 9 mm in width.

*Sepals.*—5, a blend of 147A and 183C in color, glabrous surface, tube portion about 3 mm in length and width with un-fused spreading portions about 2 mm in width and 3 mm in length, entire glandular margin, attenuate apex and fused base.

*Petals.*—5, nearly obicular in shape, un-fused, thin and papery substance, primarily entire margin (slight random notches), rounded base, rounded to broadly acute apex, about 8 mm in length and 7 mm in width, whiter than N155D in color (upper and lower surface).

*Peduncle.*—Average of 6 mm in length, <1 mm in width, 146D in color, glabrous surface.

*Pedicels.*—None (single flowers).

Reproductive organs:

*Gynoecium.*—1 pistil about 9 mm in length and 0.3 mm in width extending beyond perianth, style is 197D in color, about 8.5 mm in length, stigma is about 0.3 mm in diameter and about 197D in color, ovary is superior, oval in shape and 147C in color.

*Androcoecium.*—Average of 18 stamens, base adnate to calyx, filaments are 155A in color and blushed near base with 65A, about 4 mm in length and 0.3 mm in width, anthers are 162B in color, dorsifixed, about 0.5 mm in length and in width, no pollen was observed.

*Fruit and seed.*—Fruit; a pruinose drupe and 7 mm in length and 5 mm in width, 184B in color, glaucous surface, seed; single, 202A in color.

It is claimed:

1. A new and distinct cultivar of *Prunus* tree named 'Purple Pride' as herein illustrated and described.

* * * * *